United States Patent
Barresi et al.

(12)

(10) Patent No.: US 6,391,293 B1
(45) Date of Patent: May 21, 2002

(54) LANTHIONIZING COMPOSITIONS, SYSTEMS, AND METHODS

(75) Inventors: Frank W. Barresi, Coralville; Richard L. Antrim, Solon, both of IA (US)

(73) Assignee: Grain Processing Corporation, Muscatine, IA (US)

( * ) Notice: Subject to any disclaimer, the term of this patent is extended or adjusted under 35 U.S.C. 154(b) by 0 days.

(21) Appl. No.: 09/693,497

(22) Filed: Oct. 20, 2000

Related U.S. Application Data

(60) Provisional application No. 60/160,726, filed on Oct. 20, 1999.

(51) Int. Cl.[7] .............................. A61K 7/09; A61K 7/06
(52) U.S. Cl. .................. 424/70.2; 424/70.13; 424/70.1
(58) Field of Search ............................... 424/70.1, 70.2, 424/70.11, 70.13

(56) References Cited

U.S. PATENT DOCUMENTS

| 5,348,737 A | 9/1994 | Syed et al. |
| 5,641,477 A | 6/1997 | Syed et al. |

FOREIGN PATENT DOCUMENTS

| EP | 0 577 519 | * | 1/1994 |
| WO | WO/9936442 | | 7/1999 |
| WO | WO 00/32157 | * | 6/2000 |

* cited by examiner

Primary Examiner—Thurman K. Page
Assistant Examiner—Brian K. Seidleck
(74) Attorney, Agent, or Firm—Leydig, Voit & Mayer LTD

(57) ABSTRACT

Disclosed is a lanthionizing composition that comprises a lanthionizing agent, such as guanidine hydroxide or sodium hydroxide, and a reduced malto-oligosaccharide. Also disclosed is a method for lanthionization, the method comprising applying to the hair the lanthionizing composition of the invention.

5 Claims, No Drawings

LANTHIONIZING COMPOSITIONS, SYSTEMS, AND METHODS

RELATED APPLICATION

This application claims priority to prior provisional application Ser. No. 60/160,726, filed Oct. 20, 1999.

TECHNICAL FIELD OF THE INVENTION

The present invention relates to lanthionizing compositions and methods.

BACKGROUND OF THE INVENTION

Human hair has a variety of textures, ranging from fine to coarse, and from straight to curly. The ability to alter or change the texture of hair through chemical processes is important both for men and for women, and thus hair care products and chemical processes that can alter the texture of hair are in great demand. For example, individuals with curly hair may seek a hair care product that can straighten or "relax" the hair.

In general, hair relaxers can be purchased in the form of creams and the like, which contain active ingredients such as sodium hydroxide (lye) or guanidine hydroxide (those containing the latter are often referred to as "no-lye" relaxers). Hair fibers are composed of keratin, which is in turn composed of polypeptide chains bonded together by three types of bonds, including cystine bonds, hydrogen bonds, and salt linkages. The lanthionizing process operates primarily on the cystine bonds, and involves exposing the bonds to an alkaline relaxing solution, thereby transforming the bonds to lanthionine bonds.

Both lye-type and "no lye" type relaxers tend to decrease the tensile strength of hair considerably. Known lanthionizing products typically operate at harsh conditions, including a high pH that can degrade hair and cause hair to lose tensile strength. For example, it has been reported that hair fibers can lose as much as 55% of their tensile strength when the hair fibers are wet. U.S. Pat. No. 5,641,477 purports to disclose a process and composition for relaxing hair fibers, in which a lanthionizing agent is mixed with a hydrogenated starch hydrolyzate with a high sorbitol content and/or a sugar to form a lanthionizing composition. The presence of the carbohydrate in this composition is said to mitigate against the damage caused by the lanthionizing agent.

Another document, U.S. Pat. No. 5,548,737, purports to disclose a process in which a lanthionizing agent is applied to the hair and allowed to act on the hair for a period of time, after which the hair is treated with a deswelling composition. The deswelling composition includes a hydrogenated starch hydrolyzate with a high sorbitol content, which is said to reduce osmotic pressure in the hair fiber.

THE INVENTION

The invention provides a lanthionizing composition that comprises a lanthionizing agent, such as sodium hydroxide or guanidine hydroxide, present in an amount effective to lanthionize the hair, and a reduced malto-oligosaccharide present in an amount to impart greater tensile strength to the hair than would otherwise be achieved absent the reduced malto-oligosaccharide. The invention also encompasses a process for relaxing hair fibers, the process comprising applying to the hair fibers the lanthionizing composition of the invention.

The invention also encompasses a lanthionizing system that includes a lanthionizing composition and deswelling composition. The lanthionizing composition includes an amount of a lanthionizing agent effective to lanthionize the hair. The deswelling composition includes an amount of a reduced malto-oligosaccharide effective to deswell the hair. Also encompassed by the invention is a kit that includes the foregoing compositions. Methods for lanthionizing the hair also are encompassed by the invention.

DESCRIPTION OF THE PREFERRED EMBODIMENTS

Any lanthionizing agent known in the art or otherwise found to be suitable for lanthionizing of hair may be used in conjunction with the present invention. A typical lanthionization composition contains, as the active ingredient, about 2.4% by weight of a base such as sodium hydroxide or guanidine hydroxide, and has a pH in the range of about 12.0 to about 13.5. By lanthionization agent is also intended to refer to percursors of lanthionization agents that are mixed with another ingredient by a user to prepare the lanthionizing agent.

Provided in accordance with the invention is a composition that includes the lanthionizing agent and a reduced malto-oligosaccharide, the reduced malto-oligosaccharide being present in an amount in the range of about 0.1% to about 0.5.0% by weight of the entire lanthionizing composition. While the reduced malto-oligosaccharide species can be obtained by any suitable method, they are preferably prepared via reduction of readily available malto-oligosaccharide mixtures, e.g., as described in U.S. patent application Ser. No. 09/366,065 (corresponding to PCT/US99/01098). Malto-oligosaccharide mixtures suitable for reduction to form reduced malto-oligosaccharides are sold by Grain Processing Corporation of Muscatine, Iowa under the MALTRIN® product designation, these including, for example, MALTRIN® M040, MALTRIN® M050, MALTRIN® M100, MALTRIN® M150, and MALTRIN® M180. It will be appreciated that naturally occurring malto-oligosaccharides typically contain a mixture of a plurality of malto-oligosaccharide species. As such, the reduced malto-oligosaccharide species obtained by reduction of such naturally occurring precursors likewise will contain a plurality of reduced malto-oligosaccharide species.

Oligosaccharides can be prepared by the controlled hydrolytic cleavage of starches. In the production of such oligosaccharides, the glycoside linkages of the starch molecules are partially hydrolyzed to yield at least one oligosaccharide species, and more typically, a mixture of oligosaccharide species. Each oligosaccharide species in the mixture may be characterized by its degree of polymerization (DP), which refers to the number of saccharide units in the molecule. Each oligosaccharide species also may be characterized by its dextrose equivalent (DE), which generally indicates the proportion of aldehyde, hemiacetal or ketone terminal groups in the molecule, and which is a measure of the reducing sugar content of the oligosaccharide, expressed as a percentage of the total dry substance. The DE value and DP profile for a given oligosaccharide mixture can vary substantially, depending, for example, upon the type of starch precursor used to obtain the mixture and the conditions employed for hydrolysis of the base starch.

When a reduced malto-oligosaccharide species is obtained by reduction of a malto-oligosaccharide precursor, it will be appreciated that the DP value of the reduced product may be different from-the DP value of the precursor. The malto-oligosaccharide preferably is reduced under conditions such that when a single reduced malto-oligosaccharide species is obtained by reduction of a malto-oligosaccharide precursor, the DP value of the reduced malto-oligosaccharide species preferably is substantially preserved. Similarly, when a mixture of a plurality of reduced malto-oligosaccharide species is obtained by reduction of a mixture of a plurality of malto-oligosaccharide species, the DP profile for the product preferably is substantially retained, e.g., as described in U.S. patent application Ser. No. 09/366,065 (corresponding to PCT/US99/01098). Preferably, the reduced malto-oligosaccharide species used in accordance with the present invention has a DE of less than about 1.

The reduced malto-oligosaccharide species used in conjunction with the invention can have any suitable DP value, preferably 2 or greater and typically greater than 2 (e.g., DP of 5 or greater). In a preferred embodiment, the preserving agent includes a mixture of a plurality of reduced malto-oligosaccharide species differing at least in DP value thus defining a DP profile for the mixture. When a mixture of a plurality of reduced malto-oligosaccharide species is utilized, it is preferred that at least one of the reduced malto-oligosaccharide species has a DP greater than 5, more preferably greater than about DP 8, and most preferably greater than about DP 10.

In a preferred embodiment, at least about 80% of the reduced malto-oligosaccharide species have a DP greater than 5. More preferably at least about 60% of the reduced malto-oligosaccharide species have a DP greater than 8. Still more preferably, at least about 60% of the reduced malto-oligosaccharide species have a DP greater than 10. Most preferably, at least about 80% of the reduced malto-oligosaccharide species have a DP greater than 10. In a particularly preferred embodiment, at least about 75% of the reduced malto-oligosaccharide species in the mixture have a DP greater than 5 and at least about 40% of the reduced malto-oligosaccharide species in the mixture have a DP greater than 10.

While the reduced malto-oligosaccharide species of the preserving agent of the present invention are comprised of sugar units having different glucose linkages (typically 1,4- and 1,6-linkages) it is preferred that the majority of glucose units in the reduced malto-oligosaccharide species are 1,4-linked. When a mixture of a plurality of reduced malto-oligosaccharide species is used in the preserving agent of the present invention, it is highly preferred that and at least about 80% of the species in the mixture have a DP greater than 5.

The reduced malto-oligosaccharides used in accordance with the present invention include modified reduced malto-oligosaccharides. Examples of modified reduced malto-oligosaccharides can be found, for example, in PCT/US00/40687, describing derivatized reduced malto-oligosaccharides. Derivatized reduced malto-oligosaccharides can include, for example, reduced malto-oligosaccharides that incorporate one or more substituents or chemical modifications in one or more positions on one or more saccharide units. Such substituents can be introduced, for example, by hydroxyalkylation, oxidation, etherification, and esterification reactions. By way of example, one or more primary alcohol positions in one or more saccharide units can be oxidized to form one or more carboxylic acids. Etherification reactions can include, for example, ethoxylations, propoxylations and other alkylations, as well as reactions that can introduce a cationic charge by using reagents such as, for example, 3-chloro-2-hydryoxypropyl-trimethylammoniumchloride, or the like. Esterification reactions can include, for example, acylation reactions in which an acyl group (e.g., having from about 2 to 20 carbon atoms) is introduced to one or more saccharide units. It is contemplated that enzymatically modified reduced malto-oligosaccharides may be used in conjunction with the invention, as well as reduced malto-oligosaccharides that have been otherwise modified.

The invention also encompasses a system that includes a lanthionizing solution and a deswelling solution. The lanthionizing solution includes an amount of a lanthionizing agent effective to lanthionize the hair, as discussed above. The deswelling solution includes an amount of reduced malto-oligosaccharide effective to deswell the hair, and preferably includes an acid, such as lactic or citric acid, to neutralize caustic in the lanthionizing composition. Each solution generally includes a suitable solvent, preferably water. The system may be provided in the form of a kit that includes a first container and a second container, the first container including the lanthionizing composition and the second including the deswelling composition. The first and second containers may be contained by or within a third container, such as a package.

Also encompassed by the invention is a method for lanthionizing the hair. When the lanthionizing agent is contained in the same composition as the reduced malto-oligosaccharide, the method includes the step of applying the lanthionizing composition to the hair, waiting for a time effective to lanthionize the hair (typically about 1 minute to two hours, more typically 10–30 minutes) and at least substantially removing the composition from the hair, such as by rinsing. When the system of the invention is employed, the method includes the step of applying the lanthionizing composition., waiting for a period of time effective to lanthionize the composition, and subsequently applying the deswelling composition. The lanthionizing composition may or may not be rinsed before applying the deswelling composition. The deswelling composition may be rinsed from the hair after a period of time effective to deswell the hair, usually within about 10 minutes and typically from about 2 minutes to about 5 minutes.

The following examples further illustrate the present invention but, of course, should not be construed as in any way limiting its scope.

EXAMPLE 1

A composition comprising 2.4% by weight guanidine hydroxide, 5.0% by weight of a reduced MALTRIN® M180 prepared in accordance with the teachings of U.S. patent application Ser. No. 09/366,065, and the balance water is prepared.

EXAMPLE 2

This Example provides a lanthionizing system.

A lanthionizing solution was prepared by mixing 12.5 g of 50% sodium hydroxide in 237.5 g of distilled water (2.5% NaOH solution). Separately, as a control, a deswelling solution was prepared by mixing 162.5 g of HYSTAR 7000 a hydrogenated starch- hydrolyzate high in sorbitol obtained from Lonza corporation (70% solids) with 87.5 g of distilled water and 17.5 g of citric acid. The solution was stirred well to give a colorless mixture.

To complete the system of the invention, a deswelling solution was prepared by mixing 113.8 g of reduced malto-oligosaccharide (95% solids) with 136.2 g of distilled water and 17.5 g of citric acid. The reduced malto-oligosaccharide had a carbohydrate profile that matched that of MALTRIN® M180. The solution was stirred well to give a colorless mixture.

Hair fibers were microscopically evaluated using an Olympus BX40 Microscope at 100× magnification. Digital photos were taken using a Pixera digital camera. The hair fibers were placed on a microscope slide and two drops of the lanthionizing solution dropped onto the fiber followed by a glass cover slip. The fiber was then observed under the microscope. Total exposure of the hair fiber to the caustic solution was about 30 minutes. The hair fiber showed almost immediate signs of osmotic stress as indicated by loss in smoothness of the fiber. The appearance of many cilia type microfibers protruding from the surface of the fiber best describes the hair fiber at this point. The hair fiber was then treated with the control deswelling solution. Almost immediately, the original smoothness of the hair fiber was restored. When the process was repeated the deswelling solution that contained the reduced malto-oligosaccharide, the original smoothness of the hair fiber was again restored.

It is thus seen that the reduced malto-oligosaccharide performed as well as the HYSTAR 7000 in the deswelling solution. This is surprising given the molecular weight of the MALTRIN® as compared to the HYSTAR 7000.

All of the references cited herein, including patents, patent applications, and publications, are hereby incorporated in their entireties by reference.

While this invention has been described with an emphasis upon preferred embodiments, it will be apparent to those of ordinary skill in the art that variations of the preferred embodiments may be used and that it is intended that the invention may be practiced otherwise than as specifically described herein. Accordingly, this invention includes all modifications and equivalents encompassed within the spirit and scope of the invention as defined by the following claims.

What is claimed is:

1. A lanthionizing composition comprising:

a lanthionizing agent;

a carbohydrate, said carbohydrate comprising a mixture of a plurality of reduced malto-oligosaccharides species differing at least in degree of polymerization (DP) value, at least about 80% of the reduced malto-oligosaccharides having a DP greater than 5.

2. A lanthionizing method comprising the step of applying the composition of claim 1 to hair fibers.

3. A kit comprising:

a first container, said first container including a lanthionizing composition, said lanthionizing composition comprising a lanthionizing agent in an amount effective to lanthionize the hair; and a second container, said second container including a de-swelling composition, said de-swelling composition comprising a mixture of a plurality of reduced malto-oligosaccharide species differing a least in DP value, at least 80% of the reduced malto-oligosaccharide species having a DP greater than 5.

4. A kit according to claim 3, said first and second containers being contained by or within a third container.

5. A system comprising:

a lanthionizing composition, said lanthionizing composition comprising a lanthionizing agent in an amount effective to lanthionize the hair; and a dewswelling composition, said de-swelling composition comprising a de-swelling agent in an amount effective to de-swell the hair, said de-swelling agent comprising a mixture of a plurality of reduced malto-oligosaccharide species differing a least in DP value, at least 80% of the reduced malto-oligosaccharide species having a DP greater than 5.

* * * * *

UNITED STATES PATENT AND TRADEMARK OFFICE
CERTIFICATE OF CORRECTION

PATENT NO. : 6,391,293 B1
DATED : May 21, 2002
INVENTOR(S) : Barresi et al.

It is certified that error appears in the above-identified patent and that said Letters Patent is hereby corrected as shown below:

Column 1,
Line 38, "as55%" should read -- as 55% --

Column 2,
Line 26, "0.5.0%" should read -- 5.0% --
Line 65, "from-the" should read -- from the --

Column 4,
Line 61, "starch-hydrolyzate" should read -- starch hydrolyzate --

Signed and Sealed this

Twenty-third Day of July, 2002

Attest:

Attesting Officer

JAMES E. ROGAN
Director of the United States Patent and Trademark Office